United States Patent [19]
Atarius et al.

[11] Patent Number: 5,479,933
[45] Date of Patent: Jan. 2, 1996

[54] METHOD AND APPARATUS FOR PROCESSING ECG SIGNALS

[75] Inventors: Roozbeh Atarius, Lund; Thomas Ohlsson, Haesselby; Leif Soernmo, Lund, all of Sweden

[73] Assignee: Siemens Elema AB, Solna, Sweden

[21] Appl. No.: 264,719

[22] Filed: Jun. 23, 1994

[30] Foreign Application Priority Data

Jul. 16, 1993 [SE] Sweden .................................. 9302435

[51] Int. Cl.⁶ ............................................. A61B 5/0472
[52] U.S. Cl. ............................................. 128/696
[58] Field of Search .................................. 128/696, 703, 128/704, 706, 708

[56] References Cited

U.S. PATENT DOCUMENTS

| | | | |
|---|---|---|---|
| 4,442,459 | 12/1983 | Simson . | |
| 4,732,158 | 3/1988 | Sadeh . | |
| 4,796,638 | 1/1989 | Sasaki . | |
| 4,893,632 | 1/1990 | Armington | 128/708 |
| 5,020,540 | 6/1994 | Chamoun . | |
| 5,211,178 | 5/1994 | Kado et al. . | |
| 5,265,617 | 11/1993 | Verrier et al. | 128/704 |
| 5,277,189 | 1/1994 | Jacobs | 128/704 |
| 5,365,934 | 11/1994 | Leon et al. | 128/708 |

OTHER PUBLICATIONS

"New Technique for Detection of Changes in QRS Morphology of ECG Signals," Blumlein et al., American Journal of Physiology, vol. 244, Apr., 1983, pp. 560–566.

Primary Examiner—William E. Kamm
Assistant Examiner—Marianne Parker
Attorney, Agent, or Firm—Hill, Steadman & Simpson

[57] ABSTRACT

In a method and apparatus for processing ECG signals for the purpose of detecting low-amplitude signal structures hidden in noise in the ECG signal, the ECG signals, number of cardiac cycles are analog-to-digital converted, and QRS complexes in the converted signals are detected. The signals from at least two cardiac cycles are cross-correlated, and the correlation between these signals in time intervals which comprise at least the time intervals of the two samples is determined. An output quantity representing the degree of correlation is thus obtained, the magnitude of this quantity designating the amplitude of the signal structure in question. This magnitude can then be analyzed to determine if, and where in the signal, the signal structure arises.

19 Claims, 2 Drawing Sheets

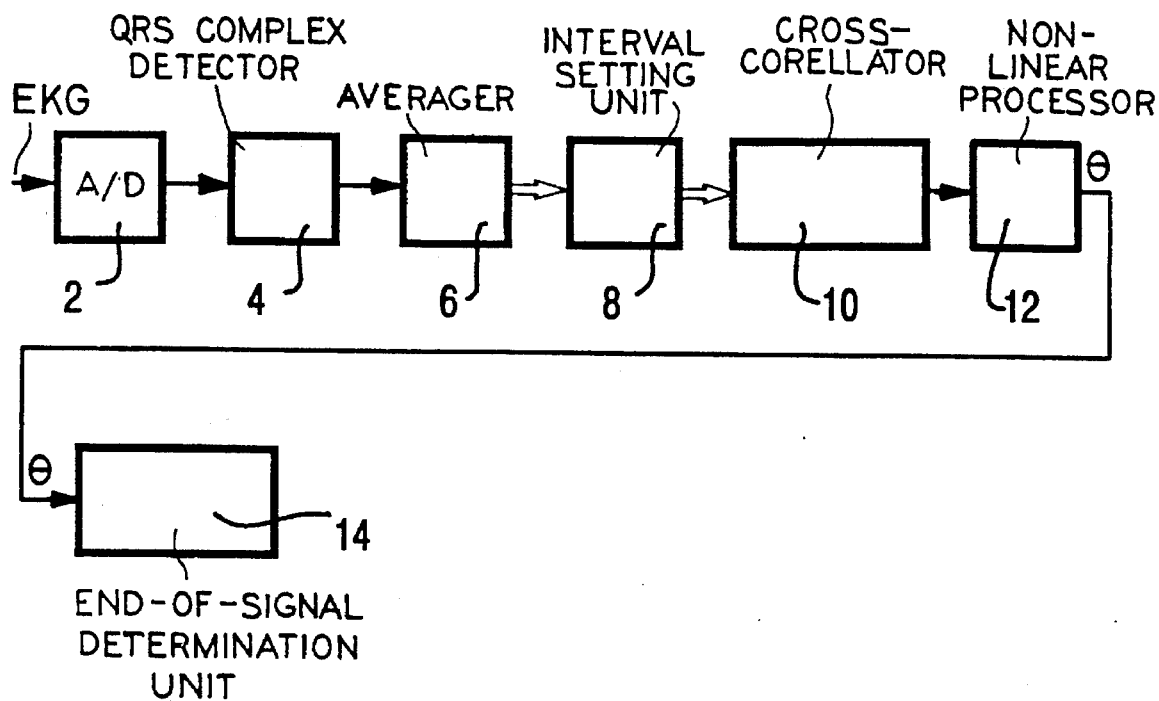
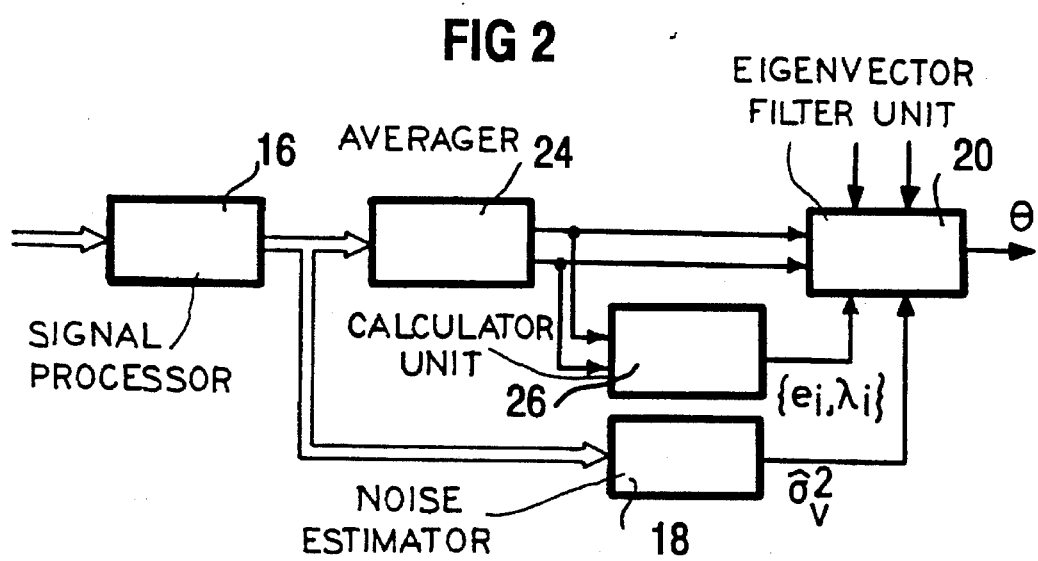

METHOD AND APPARATUS FOR PROCESSING ECG SIGNALS

BACKGROUND OF THE INVENTION

1. Field of the Invention

The present invention is directed to a method and apparatus for processing ECG signals, and in particular to such a method and apparatus for the purpose of detecting low-amplitude signal structures which are hidden in noise in the ECG signals.

2. Description of the Prior Art

It is known that low-amplitude signal structures, such as so-called late potentials, may be present in an ECG signal. Such late potentials typically have an amplitude of the order of a few μV, which usually prevents a direct, quantitative detection of such signal structures in ECG signal. Signal averaging has heretofore frequently been used to reduce the level of noise so as to more readily "expose" the low amplitude structures. In known techniques, the signal is further subjected to high pass filtering in order to eliminate the low frequency components. In U.S. Pat. No. 4,422,459, vector quantities of the X, Y and Z leads are respectively compared to a threshold value so as to determine whether late potentials are present in the signals from many of those leads. A problem with this known technique, however, is that residual noise affects the vector quantity, thereby degrading the accuracy of the threshold comparison. Moreover, important information which may be contained in the signals from an individual lead is lost when the signals are combined into a single vector quantity.

Spectral analysis of late potentials has also been proposed, however, this technique appears to have significant difficulties associated therewith, because spectral analysis of predominantly transient signals is generally complicated.

SUMMARY OF THE INVENTION

It is an object of the present invention to provide a method and apparatus which employ a statistical model to explicitly take the presence of noise in an ECG signal into account, in order to obtain a more reliable detection of low-amplitude signal structures in ECG signals.

The above object is achieved in accordance with the principles of the present invention in a method including the steps of converting the analog ECG signals into digital form over a plurality of cardiac cycles, detecting QRS complexes in the converted signals, and cross-correlating the converted signals from at least two cardiac cycles. The degree of cross-correlation between these signals over time intervals encompassing at least two cardiac cycles is determined, from which an output quantity is generated which has a magnitude designating the amplitude of the low-amplitude signal structure in question.

In an apparatus constructed in accordance with the principles of the present invention, the raw ECG signals are supplied to an analog-to-digital converter, and the converted signals are supplied to a QRS complex detector. In a cross-correlator, signals from at least two cardiac cycles are cross-correlated and the degree of cross-correlation is supplied to circuitry for generating an output signal indicative of the magnitude of the low-amplitude signal structures in question.

The present method and apparatus are based on the perception that noise is essentially uncorrelated from one cardiac cycle to the next, whereas the ECG activity of interest is repetitive.

In a further embodiment of the invention, at least two sub-average values are formed from at least the part of the ECG signals which contains the signal structure in question, from at least two different groups of cardiac cycles in the plurality of cardiac cycles. The cross-correlation between the sub-average values is then determined, an this cross-correlation is used for generating the value having the magnitude identifying the signal structure in question. This improves the possibility of separating the signal in question from the surrounding noise. In the method and apparatus of the invention, the signal from each lead is processed individually, thereby avoiding the loss of information which occurs when the respective signals from a plurality of leads are combined into a single vector quantity.

DESCRIPTION OF THE DRAWINGS

FIG. 1 is a basic block diagram of an apparatus constructed in accordance with the principles of the present invention and operating in accordance with the method of the invention.

FIG. 2 is a more detailed block diagram of functional units for identifying low-amplitude signals in the presence of noise.

DESCRIPTION OF THE PREFERRED EMBODIMENTS

Figure 3:
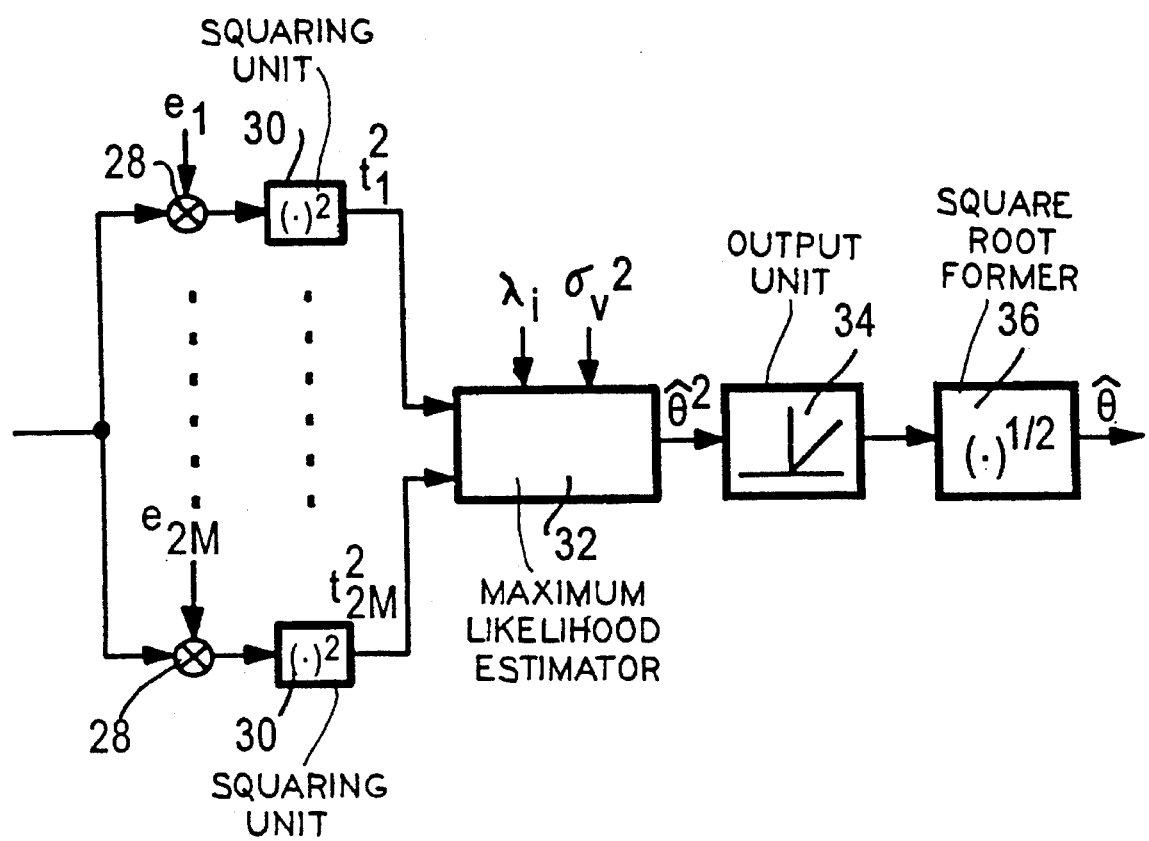
FIG. 3 is a more detailed block diagram of a so-called eigenvector filter unit and the functional blocks or subsequent non-linear signal processing in order to provide a function suitable for determining the end-of-signal of late potentials.

In the system schematically shown in FIG. 1, the recorded ECG signals (referenced EKG) are converted into digital form in an analog-to-digital converter 2, and QRS complexes in those signals are detected in a QRS complex detector 4. The output of the detector 4 is supplied to an averager 6, wherein at least two sub-average values of the signals are formed, i.e, average values of portions of the signals. An interval, or time window, is set in an interval setting unit 8 over which a cross-correlation of the signals supplied by the averager 6 takes place. The cross-correlation is undertaken in a cross-correlator 10. The cross-correlator 10 is a calculator unit which calculates the cross-correlation of the sub-average values received from the averager 6 in successive, overlapping time intervals set by the unit 8. These calculations result in the creation of a cross-correlation matrix, which determines the eigenvectors utilized for eigenvector filtering of the sub-average values, in order to filter the signals of interest out of the noise. This is described in greater detail below.

Following the cross-correlator 10, a non-linear processor 12 processes the signals filtered in the manner described above, so as to provide an output signal Θ which essentially represents the signal amplitude of the low-frequency signal structures in question. The signal Θ has a chronological course over which the magnitude of the signal Θ varies, and the signal Θ is supplied to an end-of-signal determination unit 14 which evaluates the chronological course of the signal Θ in order to identify the occurrence of an end of the signal in question.

The end-of-signal determination unit 14 may be a comparator which compares the terminal part of the signal amplitude curve of the signal Θ with a predetermined standard curve, which is successively displaced with respect to the amplitude curve for the signal Θ, so that the time at which the correlation between the standard curve and the curve for the signal $\Theta$ is highest can be determined. This time is then set as being the end time for the late potentials.

The construction and interconnection of the components 6, 8, 10 and 12 in FIG. 1 is shown in greater detail in FIG. 2. After time-synchronization of the signals from the individual cardiac cycles, the signals are edited in a signal processing unit 16, such as by high pass filtering for removing low-frequency components. In a noise estimator 18, an estimate is made of the noise 94 in the signals from the signal processor 16, and this noise estimate is supplied to an eigenvector filter unit 20.

The signals from the signal processor 16 are also supplied to an averager 24, which forms at least two sub-average values, as described above, which are then supplied to a calculator unit 26 for calculation of the cross-correlation between these sub-average values. The cross-correlation calculations result in the creation of a cross-correlation matrix, having a plurality of eigenvectors $e_i$ each having an eigenvalue $\lambda_i$ associated therewith. The sub-average values from the averager 24, the eigenvectors $e_i$ and eigenvalues $\lambda_i$ from the calculator unit 26, and the square of the noise estimate from the noise estimator 18 are all supplied to the eigenvector filter unit 20.

The signals are supplied to the averager 24 in the form of an ensemble of time-synchronized signals from a plurality of cardiac cycles. One sub-average value is formed by the signals from successive, overlapping intervals or time windows from every other signal in the ensemble, an the other sub-average value is formed by conducting a corresponding calculation for the intervening signals in the ensemble. Each time window is long enough so as to cover at least two samples.

This is only one example, however, of the manner by which the averaging can be performed. The averaging can be undertaken in a number of different ways. For example, signals having amplitudes or morphologies which differ by more than a predetermined amount from other signals in the signal ensemble may be excluded before the calculation of averages is undertaken. Moreover, the determination of the average values need not be performed in successive, overlapping intervals, as described in the above example. Averaging does not have to be performed using every other signal of the ensemble; it is also possible to divide the signals in the ensemble into two groups in some other way, with the sub-average values then being formed from the signals in the respective groups.

The details of the eigenvector filter unit 20 are shown in more detail in FIG. 3. In a series of multipliers 28, the eigenvectors of the cross-correlation matrix $e_1, e_2 \ldots e_{2M}$ are used for eigenvector-based filtering of the sub-average values. Filtering of the sub-average values with the most significant eigenvectors or only the most significant eigenvector is often sufficient. The most significant eigenvectors or eigenvector or the vectors or vector corresponding to the largest eigenvalues or eigenvalue. In practice, therefore, filtering with a limited number of eigenvectors is sufficient.

After the filtering, the signals are supplied to respective squaring units 30 connected to the outputs of each multiplier 28. The squaring units 30 have respective output signals corresponding to the quantities $t_1^2, t_2^2 \ldots t_{2M}^2$ with $t_i$ denoting the correlation between the sub-average values and the $i^{th}$ eigenvector. The outputs from the squaring units 30 are connected to a so-called maximum likelihood estimator 32, to which the noise variance $\sigma^2$ and the eigenvalues from the cross-correlation matrix are supplied from the noise estimator 18 and from the calculator unit 26, respectively.

An intermediate signal $\Theta$ is determined in the maximum likelihood estimator 32 by solving the equation $$\sum_{i=1}^{2m} \lambda_i \left\{ \frac{1}{\Theta^2 \lambda_i + \sigma_v^2} - \frac{t_i^2}{(\Theta^2 \lambda_i + \sigma_v^2)^2} \right\} = 0$$

wherein $\lambda_i$ designates the eigenvalues of the cross-correlation matrix, $\sigma_v^2$ is the statistical variance of the estimated noise, $t_i$ is the correlation between the sub-average values, $\Theta^2$ is the intermediate signal, and m is the number of samples in the interval.

Since $\Theta^2$ is not always greater than 0, the intermediate signal $\Theta^2$ is supplied to an output unit 34 having a diode-like characteristic, which supplies an output signal which is equal to 0 for negative values of $\Theta^2$, and an output signal directly proportional to $\Theta^2$ for positive $\Theta^2$ values. The square root of the output from the output unit 34 is then formed in a square root form 36. The output of the square root form 36 represents the signal amplitude $\Theta$, which indicates the amplitude of the low-amplitude signal structure in question.

The method and apparatus disclosed herein thus permit a very effective detection of low-amplitude ECG activity in a noisy environment, with correlation both in time and over an ensemble cardiac cycles being taken into account.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method for processing an ECG signal containing noise and low-amplitude signal structures, comprising the steps of:

detecting respective ECG signals from a plurality of cardiac cycles;

converting said ECG signals into digital signals;

detecting QRS complexes in said digital signals;

time-synchronizing digital signals from at least two cardiac cycles;

cross-correlating the time-synchronized digital signals over a time interval encompassing at least two cardiac cycles to obtain a cross-correlation quantity having a magnitude;

estimating a level of said noise in said ECG signals from each heart cycle;

compensating for said level of noise in the cross-correlation of said time-synchronized signals; and generating a signal indicative of said low-amplitude signal structures from said cross-correlation quantity.

2. A method as claimed in claim 1 comprising the additional step of forming two sub-average values from at least a part of said ECG signals containing said low-amplitude signal structures from at least two different groups of cardiac cycles in said plurality of cardiac cycles, and employing said sub-average values as said signals in the cross-correlation.

3. A method as claimed in claim 2 wherein the step of forming at least two sub-average values comprises forming n sub-average values with n>2, from signals in respective groups of cardiac cycles respectively formed by cardiac cycles designated in sequence as cardiac cycles 1, n+1, 2n+1 ..., and 2, n+2, 2n+2 ... n, 2n, 3n ... groups of cardiac cycles.

4. A method as claimed in claim 3 comprising the step of cross-correlating said sub-average values in successive, overlapping time intervals.

5. A method as claimed in claim 4 comprising the step of filtering said sub-average values dependent on the magnitude of the cross-correlation of said sub-average values to obtain filtered values, and non-linearly processing said filtered values for generating a function representing the amplitude of said low-amplitude signal structures.

6. A method as claimed in claim 5 comprising the additional step of compensating for noise in said filtered values simultaneously with said non-linear processing.

7. A method as claimed in claim 3 comprising the additional step of generating a cross-correlation matrix from the cross-correlation of said sub-average values and filtering said sub-average values based on eigenvectors determined from said cross-correlation matrix.

8. A method as claimed in claim 5 wherein the step of non-linearly processing said filtered values comprises squaring said filtered values, calculating a signal power associated with the squared filtered values, and calculating the signal amplitude of said low-amplitude signal structures from said signal power.

9. A method as claimed in claim 8 comprising the additional step of generating a signal amplitude curve of said low-amplitude signal structures from said magnitude of said output quantity and comparing said curve to a standard curve for identifying an end point of a signal structure.

10. A method as claimed in claim 1 wherein said low-amplitude signal structures comprise late potentials in said ECG signals.

11. An apparatus for processing an ECG signal containing noise and low-amplitude signal structures, comprising:
    means for detecting respective ECG signals from a plurality of cardiac cycles;
    means for converting said ECG signals into digital signals;
    means for detecting QRS complexes in said digital signals;
    means for time-synchronizing digital signals from at least two cardiac cycles;
    means for cross-correlating the time-synchronized digital signals over a time interval encompassing at least two cardiac cycles to obtain a cross-correlation quantity having a magnitude;
    means for estimating a level of said noise in said ECG signals from each heart cycle;
    means for compensating for said level of noise in the cross-correlation of said time-synchronized signals; and
    means for generating a signal indicative of said low-amplitude signal structures from said cross-correlation quantity.

12. An apparatus as claimed in claim 11 further comprising means for forming two sub-average values from at least a part of said ECG signals containing said low-amplitude signal structures from at least two different groups of cardiac cycles in said plurality of cardiac cycles, and said means for cross-correlating employing said sub-average values as said signals in the cross-correlation.

13. An apparatus as claimed in claim 12 wherein said means for cross-correlating comprises means for cross-correlating said sub-average values in successive, overlapping time intervals.

14. An apparatus as claimed in claim 13 further comprising
    means for filtering said sub-average values dependent on the magnitude of the cross-correlation of said sub-average values to obtain filtered values; and
    means for non-linearly processing said filtered values for generating a function representing the amplitude of said low-amplitude signal structures.

15. An apparatus as claimed in claim 14 wherein said means for non-linearly processing said filter values comprises means for compensating for noise in said filtered values simultaneously with said non-linear processing.

16. An apparatus as claimed in claim 15 wherein said means for cross-correlating comprises means for generating a cross-correlation matrix from the cross-correlation of said sub-average values and wherein said means for filtering comprises means for filtering said sub-average values based on eigenvectors determined from said cross-correlation matrix.

17. An apparatus as claimed in claim 16 wherein said means for non-linearly processing said filtered values comprises means for squaring said filtered values, means for calculating a signal power associated with the squared filtered values, and means for calculating the signal amplitude of said low-amplitude signal structures from said signal power.

18. An apparatus as claimed in claim 17 wherein said means for estimating a level of said noise in said ECG signals comprises a maximum likelihood estimator which solves the following maximum likelihood equation $$\sum_{i=1}^{2m} \lambda_i \left\{ \frac{1}{\theta^2 \lambda_i + \sigma_v^2} - \frac{t_i^2}{(\theta^2 \lambda_i + \sigma_v^2)^2} \right\} = 0$$

wherein $\lambda_i$ are eigenvalues of said cross-correlation matrix, $\sigma_v^2$ is the statistical variance of the estimated noise, $t_i$ is the correlation between the sub-average values, $\Theta^2$ is said signal power, and m is the number of samples in the interval.

19. An apparatus as claimed in claim 11 further comprising means for generating a signal amplitude curve of said low-amplitude signal structures from said magnitude of said output quantity and for comparing said curve to a standard curve for identifying an end point of a signal structure.

* * * * *